(12) United States Patent
Bullard et al.

(10) Patent No.: US 10,919,831 B1
(45) Date of Patent: *Feb. 16, 2021

(54) METHOD OF PEROXYLACTIC ACID PRODUCTION AND USE FOR REDUCTION IN MICROBIAL ACTIVITY IN FOOD PRODUCT PROCESSING

(71) Applicant: Zee Company, Inc., Chattanooga, TN (US)

(72) Inventors: Robert C. Bullard, Signal Mountain, TN (US); Jonathon R. Bullard, Chattanooga, TN (US); James A. Faller, Chattanooga, TN (US); A. Rider Barnum, Hixon, TN (US)

(73) Assignee: Zee Company, Inc., Chattanooga, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/984,770

(22) Filed: Aug. 4, 2020

Related U.S. Application Data

(63) Continuation of application No. 16/681,171, filed on Nov. 12, 2019, now Pat. No. 10,745,338.

(60) Provisional application No. 62/760,482, filed on Nov. 13, 2018.

(51) Int. Cl.
*C07C 51/02* (2006.01)

(52) U.S. Cl.
CPC .................................... *C07C 51/02* (2013.01)

(58) Field of Classification Search
None
See application file for complete search history.

(56) References Cited

U.S. PATENT DOCUMENTS

| 4,617,090 A | 10/1986 | Chum et al. |
| 5,632,676 A | 5/1997 | Kurschner et al. |
| 10,745,338 B1 | 8/2020 | Bullard et al. |

OTHER PUBLICATIONS

Application and File History for U.S. Appl. No. 16/681,171 (now U.S. Pat. No. 10,745,338) filed Nov. 12, 2019, inventors Bullard et al.

*Primary Examiner* — Sudhakar Katakam
*Assistant Examiner* — Jennifer C Sawyer
(74) *Attorney, Agent, or Firm* — Patterson Thuente Pedersen, P.A.

(57) ABSTRACT

A method for producing an aqueous equilibrium peroxylactic acid solution by reaction mixing lactic acid, hydrogen peroxide, water, one or more optional acid catalysts and one or more optional sequestering agents in a vessel over a period of time while maintaining the temperature of the solution at a temperature below about 100° C. The aqueous equilibrium peroxylactic acid solution can be used for reducing the bacterial count on a protein food product during processing.

32 Claims, No Drawings

METHOD OF PEROXYLACTIC ACID PRODUCTION AND USE FOR REDUCTION IN MICROBIAL ACTIVITY IN FOOD PRODUCT PROCESSING

CROSS-REFERENCE TO RELATED APPLICATIONS

The present application is a continuation of U.S. application Ser. No. 16/681,171 filed Nov. 12, 2019 which claims the benefit of U.S. Provisional Application No. 62/760,482 filed Nov. 13, 2018, which is hereby incorporated herein in its entirety by reference.

FIELD OF THE INVENTION

The present invention relates to a method of producing an aqueous equilibrium peroxylactic acid solution composition for reducing the bacterial count on a food product during processing, more particularly a method of producing an equilibrium peroxylactic acid composition for use in soaking, dipping, chilling, spraying, quenching, rinsing and/or washing processes of a protein food product, such as red meat, poultry, pork, fish, eggs, seafood and nuts.

BACKGROUND OF THE INVENTION

The world population has grown to point where mass production of the foods that we consume is no longer a luxury but a requirement. Local farmers, providing food and food products directly to the marketplace, cannot meet the demands of modern society. The food supply chain now incorporates very large, complex farms and high speed and very high volume processing plants to satisfy the need for mass processing and production of food. Maintaining a safe food supply chain relies on the dedication of those working in the supply chain, the processing plants and also on the third party oversight of various Federal agencies whose regulations support and mandate food safety.

With two major exceptions, the physical process of taking an animal from the farm to the consumer has changed very little over time. The introduction of refrigeration, and the implementation of various chemistries to help maintain sanitary conditions and to control microbiology, has given modern food processors an advantage not enjoyed by food producers of a century ago. Refrigeration and chemical intervention practices have become an integral part of food processing facility operations. These technologies have enabled the high speed, high volume output of the large processing facilities that could not have been possible in times past without significant concern for consumer safety. With large scale and continuous processing methods being employed by large processors of protein products, or any other product that is susceptible to microbiological contamination, the concern for the control of microbiology and the safety of the food supply chain is of paramount importance.

Another concern, as the demand for food products increases, is the impact on natural resources created by this demand. The ecological impact is directly affected by this growth and therefore new processes must be developed to reduce the impact any given process has on the environment. The ecological impact that a food processing plant has on the environment is no longer a passing concern but a major part of operations and planning. Entire processes are built around the control and conservation of natural resources such as water. Older, outdated and less efficient processes are being replaced at significant cost with more efficient and less wasteful processes that maximizes the utility of available resources. No longer can a plant operate without concern for the conservation and sustainability of natural resources.

To insure that the food supply chain in modern society is maintained at the highest levels of safety for the consumer, the plant's employees, and the overall environment, there are federal agencies that monitor the processors operations so that a continually safe food supply is assured and the environmental impact and utilization of natural resources is as safe and efficient as possible.

Modern food processing methods are scrutinized by government agencies to ensure compliance with safe handling and processing guidelines designed to minimize issues of food safety in the supply chain Regulations and routine inspections of systems and processes by Federal agencies such as the USDA, EPA and OSHA, mandate a government-industry alliance that helps ensure that every effort is made to deliver the safest product possible to the consumer. The FDA also regulates food contact substances, such as chemical intervention solutions used during processing of food products to reduce microbial activity.

Very innovative approaches to the systems and methods used in processing facilities have been implemented to create profits for industry while maintaining low consumer cost of the final product. As new processes are developed, the federal agencies that have jurisdiction over any particular process are called upon to review the new approach and to ensure that the new innovation meets the current guidelines for safety. The higher the processors output, the higher the risk of microbiological contamination, and therefore the more innovative the processor must be to combat this ever present threat to the food chain safety. As new risks are found, federal guidelines become more stringent.

Large scale refrigeration systems, used to help control microbial growth in various processing applications, have helped the food processing industry to remain in compliance with food safety goals. Refrigeration applications and processes are implemented at various locations in the processing operation to ensure maximization of microbiology control and shelf life. Depending on the particular food product being processed—beef, pork, poultry, fish, eggs, nuts, fruits, vegetables, for example—and the particular operation taking place, various methods of achieving this reduction in product temperature are employed. In poultry processing for example, submersion in large chilled water baths is the allowed and preferred method for the rapid reduction in carcass temperature after evisceration.

Immersion chilling has a benefit of an increased "washing effect" which lowers the total microbial load on poultry; however, it is also a potential place for cross contamination to occur. In order to control microbiology in chiller tanks, it is a typical practice to add specialized chemistry to the tanks throughout the processing day. This specialized chemistry, known in the industry as intervention solutions kill or provide a $\log_{10}$ reduction in the amount of any unwanted microorganisms. There are several antimicrobials that are approved and effective for use in the chiller to decrease pathogens, including, for instance, chlorine, peroxyacetic acid ("PAA"), CPC, organic acids, TSP, acidified sodium chlorite and chlorine dioxide. Because chiller tanks are often quite voluminous, the amount of antimicrobials needed can be quite high to provide a desired $\log_{10}$ reduction in the amount of any unwanted microorganisms.

PAA, which is also sometimes called peroxyacetic acid, is a peroxycarboxylic acid and is a well known chemical for its strong oxidizing potential, has the molecular formula $CH_3COOOH$, and has a molecular structure as follows:

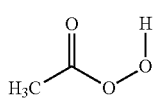

An equilibrium peroxyacetic acid solution is produced from an equilibrium mixture of hydrogen peroxide, acetic acid and water ("equilibrium PAA solution"), which often uses an acid catalyst, e.g., sulfuric acid.

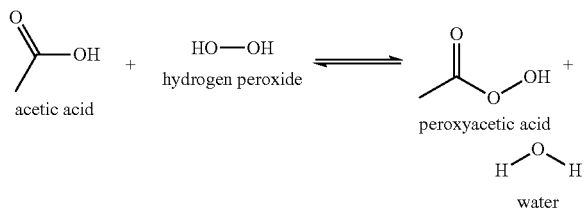

U.S. Pat. No. 5,632,676, which pertains to the application of equilibrium PAA solutions to fowl at an application concentration of about 100 ppm to about 2000 ppm, discloses such equilibrium solutions having a pH around 3. While the production of equilibrium PAA solutions is well known, using such methods for the production of other peroxycarboxylic acids does not readily transfer into stable equilibrium solutions for all peroxycarboxylic acids. Instead, the normal PAA production for other peroxycarboxylic acids results in weak and unstable product.

Besides immersion chilling, food products may undergo other processes before being provided to a consumer, such as being dipped, rinsed, washed, sprayed, quenched, soaked, and the like in a chemical intervention solution to reduce or facilitate elimination of the risk of microbial contamination. The use of such chemical intervention solutions in such various food processing processes has recently brought to question the health risks of human exposure to such solutions during food processing, including PAA, which has a distinct, pungent odor.

Ideally, a chemical intervention solution used in such food processing processes or systems will have several important properties in addition to its antimicrobial efficacy, including no technical effect on the final food product, reduced or odor free and/or ability not to transfer undesirable odors onto the food product, composed of components that do not interfere with the food wholesomeness or affect a human should there be incidental ingestion, and be composed of components that are nontoxic and environmentally friendly.

Despite there being various chemical intervention solutions in the market, there is a need in the industry for improved antimicrobial compositions that are stabile and efficiently and cost-effectively reduce microbial contamination of food products during processing.

SUMMARY OF THE INVENTION

In some aspects of the present invention, a process for producing an aqueous equilibrium peroxylactic acid solution composition that comprises slowly mixing a starting composition comprising lactic acid, hydrogen peroxide, deionized water, one or more optional acid catalysts and one or more optional sequestering agents in a vessel and allowing the components to react over a period of time while maintaining the temperature of the solution greater than about 20° C. and below about 100° C.

In some aspects, a molar ratio of hydrogen peroxide to lactic acid in the aqueous equilibrium peroxylactic acid solution is at least 3:1. In some aspects, the molar ratio is from about 3:1 to about 6:1 of hydrogen peroxide to lactic acid.

In some aspects, the amount of lactic acid is about 19.8 to about 29.6 weight percent, more preferably about 21.0 to about 28.4 weight percent, more preferably about 22.2 to about 27.2 weight percent, and even more preferably about 23.5 to about 25.9 weight percent, of the total weight percent of the starting composition.

In some aspects, the amount of hydrogen peroxide is about 33.6 to about 50.4 weight percent, more preferably about 35.7 to about 48.3 weight percent, more preferably about 37.8 to about 46.2 weight percent, and even more preferably about 39.9 to about 44.1 weight percent, of the total weight percent of the starting composition.

In some aspects, the acid catalyst comprises one or more inorganic acid to drive the components to the equilibrium peroxylactic acid composition. In some aspects, the one or more inorganic acid comprises phosphoric acid, sulfuric acid, sulfamic acid, hydrochloric acid, nitric acid, boric acid, or mixtures thereof. In some other aspects, the one or more inorganic acid comprises phosphoric acid. In some other aspects, the one or more inorganic acid comprises sulfuric acid. In some other aspects, the one or more inorganic acid comprises phosphoric acid and sulfuric acid.

In some aspects, the one or more inorganic acids is present in an amount from greater than 0 up to about 17.0 weight percent, more preferably greater than 0.05 up to about 15.0 weight percent, more preferably greater than about 0.1 up to about 10.0 weight percent, more preferably greater than about 0.2 up to about 4.5 weight percent, and even more preferably greater than about 0.25 up to about 3.5 weight percent, of the total weight percent.

In some aspects, the one or more inorganic acid comprises phosphoric acid present in an amount from greater than 0 up to about 10.0 weight percent, more preferably greater than 0.05 up to about 5.0 weight percent, more preferably greater than about 0.1 up to about 3.0 weight percent, more preferably greater than about 0.2 up to about 2.5 weight percent, and even more preferably greater than about 0.25 up to about 2.0 weight percent, of the total weight percent of the starting composition.

In some aspects, the one or more inorganic acid comprises sulfuric acid present in an amount from greater than 0 up to about 10.0 weight percent, more preferably greater than 0.05 up to about 5.0 weight percent, more preferably greater than about 0.1 up to about 3.0 weight percent, more preferably greater than about 0.2 up to about 2.5 weight percent, and even more preferably greater than about 0.25 up to about 2.0 weight percent, of the total weight percent of the starting composition.

In some aspects, the one or more inorganic acid comprises phosphoric acid and sulfuric acid in an amount greater than 0 up to about 17.0 weight percent, more preferably greater than 0.05 up to about 15.0 weight percent, more preferably greater than about 0.1 up to about 10.0 weight percent, more preferably greater than about 0.2 up to about 4.5 weight percent, and even more preferably greater than about 0.25 up to about 3.4 weight percent, of the total weight percent.

In some aspects, the one or more sequestering agents comprises etidronic (HEDP) acid (1-Hydroxyethylidene-1, 1-diphosphonic acid), ATMPT (Aminotris(methylenephosphonic acid), EDTMP (Ethylenediaminetetra(methylenephosphonic acid), TDTMP (Tetramethylenediaminetetra (methylenephosphonic acid), HDTMP (Hexamethylenediaminetetra(methylenephosphonic acid), DTPMP (Diethylenetriaminepenta(methylenephosphonic acid), 2-phosphonobutane 1,2,4-tricarboxylic acid, Nitrilotrimethylenetris (diphosphonic acid), dipicolinic acid, or mixtures thereof.

In some aspects, the one or more sequestering agents is present in an amount from greater than 0 up to 8.0 weight percent, more preferably greater than about 0.01 up to about 4.0 weight percent, preferably greater than about 0.02 up to about 2.0 weight percent, preferably greater than about 0.03 up to about 1.0 weight percent, more preferably greater than about 0.04 up to about 0.5 weight percent, even more preferably greater than about 0.05 up to about 0.15 weight percent, of the total weight percent.

In some aspects, the one or more sequestering agents comprises HEDP In some aspects, the one or more sequestering agents comprising HEDP is present in an amount from greater than 0 up to 0.2 weight percent, more preferably greater than about 0.01 up to about 0.175 weight percent, even more preferably greater than about 0.02 up to about 0.15 weight percent, of the total weight percent of the starting composition.

In some aspects, the starting composition comprising lactic acid, hydrogen peroxide, deionized water, optionally one or more acid catalysts and optionally one or more sequestering agents is reacted for period of time up to about 7 days, preferably at least an hour up to 7 days, preferably greater than 3 hours up to about 7 days, preferably greater than about 24 hours up to about 7 days, preferably greater than about 48 hours up to about 7 days, and even more preferably about 3 days to about 7 days, to form the aqueous equilibrium peroxylactic acid solution. In some aspects, the starting composition comprising lactic acid, hydrogen peroxide, deionized water, optionally one or more acid catalysts and optionally one or more sequestering agents is agitated while each component is added into the vessel and continued for about 3 hours to about 6 hours after the last component is added into the vessel, and the starting composition is then continually mixed for a period of time while the starting composition reacts to form an aqueous equilibrium peroxylactic acid solution, wherein the period of time is at least 24 hours up to about 7 days, in some aspects up to about 6 days, in some aspects up to about 5 days, in some aspects up to about 4 days, in some aspects up to about 3 days, in some aspects up to about 48 hours. In some aspects, the period of time is greater than about 24 hours up to about 7 days, preferably between about 2 days and 7 days, and in some aspects between about 2 days and about 4 days.

In some aspects, the temperature is maintained below about 100° C. while the starting composition comprising lactic acid, hydrogen peroxide, deionized water, one or more optional acid catalysts and one or more optional sequestering agents react to achieve equilibrium, preferably below about 90° C., preferably below about 80° C., preferably below about 70° C., preferably below about 60° C., even more preferably below about 55° C. In some aspects, the temperature is maintained between about 1° C. and about 100° C., preferably between about 20° C. and about 100° C., preferably between about 25° C. and about 90° C., preferably between about 30° C. and about 80° C., preferably between about 35° C. and about 70° C., preferably between about 40° C. and about 60° C., even more preferably between about 45° C. and about 55° C.

In some aspects, the resulting peroxylactic acid solution produced by the process of the present invention comprises peroxylactic acid, hydrogen peroxide, lactic acid, and water in an equilibrium solution.

In certain aspects, the aqueous equilibrium peroxylactic acid solution will have peroxylactic acid present in an amount of about 2.5 to about 15.0 weight percent, preferably about 5.0 to about 12.5 weight percent, preferably about 9.0 to about 11.5 weight percent, more preferably about 9.5 to about 11.0 weight percent, of the total weight percent.

In certain aspects, the aqueous equilibrium peroxylactic acid solution will have hydrogen peroxide present in an amount of about 19.0 to about 30.0 weight percent, preferably about 20.5 to about 28.0 weight percent, preferably about 22.0 to about 27.0 weight percent, more preferably about 23.0 to about 25.5 weight percent, of the total weight percent of the solution.

In certain aspects, the aqueous equilibrium peroxylactic acid solution will have lactic acid present in an amount of about 1.0 to about 10.0 weight percent, preferably about 2.0 to about 5.0 weight percent, preferably about 2.5 to about 4.5 weight percent, more preferably about 3.0 to about 4.0 weight percent, of the total weight percent of the solution.

In certain aspects where one or more optional acid catalysts are present during the reaction, the equilibrium peroxylactic acid solution will comprise the respective one or more acid catalysts. In certain aspects, the aqueous equilibrium peroxylactic acid solution produced with one or more inorganic acid catalysts will have the one or more inorganic acid catalysts present in an amount greater than 0 up to about 8.0 weight percent, more preferably greater than about 0.1 up to about 4.0 weight percent, more preferably greater than about 0.25 up to about 3.75 weight percent, and even more preferably greater than about 0.3 up to about 3.5 weight percent, of the total weight percent of the solution.

In certain aspects, the aqueous equilibrium peroxylactic acid solution produced with sulfuric and/or phosphoric acid will have each of the inorganic acid catalysts present in an amount greater than 0 up to about 4.2 weight percent, more preferably greater than about 0.1 up to about 3.9 weight percent, more preferably greater than about 0.25 up to about 3.75 weight percent, and even more preferably greater than about 0.3 up to about 3.5 weight percent, of the total weight percent. In certain aspects other aspects, the aqueous equilibrium peroxylactic acid solution produced with sulfuric and/or phosphoric acid will have each of the inorganic acid catalysts present in an amount greater than 0 up to about 2.5 weight percent, more preferably greater than about 0.1 up to about 2.25 weight percent, more preferably greater than about 0.25 up to about 2.0 weight percent, and even more preferably greater than about 0.3 up to about 1.9 weight percent, of the total weight percent of the solution.

In certain aspects where one or more optional sequestering agents are present during the reaction, the equilibrium peroxylactic acid solution will comprise the respective one or more sequestering agents. In certain aspects, the aqueous equilibrium peroxylactic acid solution produced with one or more sequestering agents will have the one or more sequestering agents present in an amount from greater than 0 up to 0.1 weight percent, more preferably greater than about 0.02 up to about 0.08 weight percent, even more preferably greater than about 0.03 up to about 0.075 weight percent, of the total weight percent of the solution.

In certain aspects, the aqueous equilibrium peroxylactic acid solution produced with HEDP will have the sequestering agent present in an amount from greater than 0 up to 0.1 weight percent, more preferably greater than about 0.02 up to about 0.08 weight percent, even more preferably greater than about 0.03 up to about 0.075 weight percent, of the total weight percent of the solution.

In certain aspects, the peroxylactic acid in the aqueous equilibrium peroxylactic acid solution exhibits less than 20% degradation over a period of at least 30 days, preferably at least 45 days, preferably at least 60 days, even more preferably at least 90 days. In certain aspects, the peroxylactic acid in the aqueous equilibrium peroxylactic acid solution exhibits less than 15% degradation over a period of at least 30 days, preferably at least 45 days, preferably at least 60 days, even more preferably at least 90 days. In certain aspects, the peroxylactic acid in the aqueous equilibrium peroxylactic acid solution exhibits less than 10% degradation over a period of at least 30 days, preferably at least 45 days, preferably at least 60 days, even more preferably at least 90 days.

In certain aspects, the aqueous equilibrium peroxylactic acid solution produced by the process of the present invention is used in soaking, dipping, chilling, spraying, quenching, rinsing and/or washing a food product.

In some aspects, the aqueous equilibrium peroxylactic acid solution produced by the present invention is applied to a food product at a concentration of the peroxylactic acid between about 5 ppm and about 2000 ppm, in some aspects between about 5 ppm and about 1000 ppm, in some aspects, in some aspects between about 5 ppm and about 500 ppm, in some aspects, in some aspects between about 5 ppm and about 250 ppm, in some aspects between about 5 ppm and about 100 ppm, in some aspects between about 10 ppm and about 1000 ppm, in some aspects between about 20 ppm and about 100 ppm.

In some aspects, the aqueous equilibrium peroxylactic acid solution produced by the present invention is applied to a food product at a concentration of the peroxylactic acid greater than about 5 ppm and up to about 2000 ppm, in some aspects up to about 1500 ppm, in some aspects up to about 1000 ppm, in some aspects up to about 500 ppm, in some aspects up to about 250 ppm, in some aspects up to about 100 ppm, in some other aspects up to about 75 ppm, and in some aspects up to about 50 ppm.

In some aspects, the product chosen is red meat, poultry (e.g., chicken, turkey, duck), pork, fish, eggs, seafood, or nuts.

In some aspects, a poultry carcass is immersion chilled in the aqueous equilibrium peroxylactic acid solution at a concentration of the peroxylactic acid between about 5 ppm and about 2000 ppm, in some aspects between about 10 ppm and about 1500 ppm, in some aspects between about 20 ppm and about 1000 ppm, in some aspects between about 25 ppm and about 500 ppm, and in some other aspects between about 30 ppm and about 100 ppm. In some aspects, the poultry carcasses is immersion chilled in the aqueous equilibrium peroxylactic acid solution at a concentration of the peroxylactic acid greater than about 5 ppm and up to about 2000 ppm, in some aspects up to about 1500 ppm, in some aspects up to about 1000 ppm, in some aspects up to about 500 ppm, in some aspects up to about 250 ppm, in some aspects up to about 100 ppm, in some other aspects up to about 75 ppm, and in some aspects up to about 50 ppm.

In some aspects, an animal carcass is sprayed with the aqueous equilibrium peroxylactic acid solution at a concentration of the peroxylactic acid between about 5 ppm and about 2000 ppm, in some aspects between about 10 ppm and about 1500 ppm, in some aspects between about 20 ppm and about 1000 ppm, in some aspects between about 25 ppm and about 500 ppm, and in some other aspects between about 30 ppm and about 100 ppm. In some aspects, the animal carcass is sprayed with the aqueous equilibrium peroxylactic acid solution at a concentration of the peroxylactic acid between about 5 ppm and up to about 2000 ppm, in some aspects up to about 1500 ppm, in some aspects up to about 1000 ppm, in some aspects up to about 500 ppm, in some aspects up to about 250 ppm, in some aspects up to about 100 ppm, in some other aspects up to about 75 ppm, and in some aspects up to about 50 ppm.

In some aspects, the aqueous equilibrium peroxylactic acid solution produced by the present invention has a pH greater than 0.5 and less than about 3.0, preferably less than about 2.75, preferably less than about 2.5, preferably less than about 2.25, preferably less than about 2.0, preferably less than about 1.75, preferably less than about 1.5, preferably less than about 1.25, preferably less than about 1.0, and in some aspects preferably less than about 0.75.

In some aspects, the aqueous equilibrium peroxylactic acid solution produced by the present invention is stored at a temperature between about 15° C. and about 25° C., preferably about 18° C. and about 24° C., such that the aqueous equilibrium peroxylactic acid solution exhibits less than 20% degradation, more preferably less than 15% degradation, more preferably less than 10% degradation, and more preferably less than 5% degradation over a period of at least 30 days, preferably at least 45 days, preferably at least 60 days, even more preferably at least 90 days.

The above summary is not intended to describe each illustrated embodiment or every implementation of the subject matter hereof.

DETAILED DESCRIPTION

In the present invention, the inventors have surprisingly discovered a process for producing an aqueous equilibrium peroxylactic acid solution having an increased stability while having an acceptable degradation profile when applied to an organic food product. The increased stability of use of the aqueous equilibrium peroxylactic acid solution of the present invention is desirable in that it provides the option of using less of the antimicrobial solution to achieve the same desired antimicrobial effect of comparable antimicrobial solutions, such as peroxyacetic acid. The increased stability of use of the aqueous equilibrium peroxylactic acid solution of the present invention also provides the advantage of requiring less of the antimicrobial solution in make-up solutions as the concentration of the antimicrobial solutions are depleted during food processing, as well as, the amount of make-up water required to maintain acceptable antimicrobial concentrations in food processing applications, such as in dip tank and immersion chilling tank applications.

The process for producing an aqueous equilibrium peroxylactic acid solution having the following formula generally comprises reacting a 1:1 molar ratio of 50% hydrogen peroxide with lactic acid in deionized water while maintaining temperature control greater than about 20° C. and below about 100° C., with the optional addition of one or more acid catalysts and the optional addition of one or more optional sequestering agents:

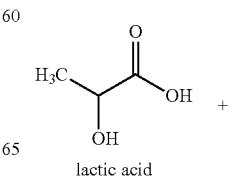

lactic acid

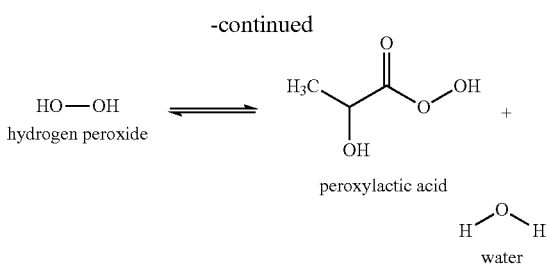

In some aspects, the process of producing an aqueous equilibrium peroxylactic acid solution comprises combining a quantity sufficient of deionized water with the lactic acid and then after the lactic acid is blended with the deionized water mixing the mixture such that agitation is provided while one or more optional sequestering agents, one or more optional acid catalysts, and hydrogen peroxide is added to the mixture. In some aspects, it is desirable that the quantity sufficient of deionized water is blended with the lactic acid before the remaining ingredients are added, and in some preferred aspects the one or more optional sequestering agents, one or more optional acid catalysts, and hydrogen peroxide are sequentially added. In some aspects, the mixture is continued to be agitated by mixing for at least about 30 minutes up to about 6 hours after the hydrogen peroxide has been added. With continued mixing, the temperature of the mixture is then heat controlled by maintaining the temperature below about 100° C. while the starting composition comprising lactic acid, hydrogen peroxide, deionized water, one or more optional acid catalysts and one or more optional sequestering agents react to achieve equilibrium over a period of about 24 hours up to about 7 days.

In some aspects, the temperature of the mixture is heat controlled at a temperature preferably below about 90° C., preferably below about 80° C., preferably below about 70° C., preferably below about 60° C., even more preferably below about 55° C. In some aspects, the temperature is maintained between about 1° C. and about 100° C., preferably between about 20° C. and about 95° C., preferably between about 25° C. and about 90° C., preferably between about 30° C. and about 80° C., preferably between about 35° C. and about 70° C., preferably between about 40° C. and about 60° C., even more preferably between about 45° C. and about 55° C. In some aspects, the temperature of the mixture is heat controlled by heating the mixture, cooling the mixture and/or allowing the mixture to stay within the desired temperature range while the starting formula components react to form the equilibrium peroxylactic acid solution.

After equilibrium is established, the temperature range in production and storage is maintained between about 15° C. and about 25° C., preferably about 18° C. and about 24° C. to help control equilibrium establishment and maintain product stability.

The raw materials used in the production of the product are preferably high-grade, commercially available lactic acid, hydrogen peroxide, and when present the one or more optional sequestering agents, such as HEDP, and the one or more optional acid catalysts, such as sulfuric and/or phosphoric acid.

In some aspects, the reaction using one or more optional acid catalysts generally takes about 24 hours up to about 7 days to achieve equilibrium. The use of one or more optional sequestering agents chelates the metals that catalyze the decomposition of hydrogen peroxide. The peroxylactic acid product is stabilized with excess hydrogen peroxide, lactic acid, and being in an aqueous solution.

In some aspects, the molar ratio of hydrogen peroxide to lactic acid is at least 3:1 (hydrogen peroxide:lactic acid). In some aspects, the molar ratio is from about 3:1 to about 6:1, in some aspects about 3.1:1 to about 5:1, in some aspects about 3.2:1 to about 4.5:1, and in some other aspects about 3.3:1 to about 4.0:1, hydrogen peroxide to lactic acid to provide improved stability of the peroxylactic acid product.

The peroxylactic acid in the aqueous equilibrium peroxylactic acid solution of the present invention exhibits less than 20% degradation over a period of at least 30 days, preferably at least 45 days, preferably at least 60 days, even more preferably at least 90 days while maintained at a temperature between about 15° C. and about 25° C., preferably about 18° C. and about 24° C. In certain aspects, the peroxylactic acid in the aqueous equilibrium peroxylactic acid solution exhibits less than 15% degradation over a period of at least 30 days, preferably at least 45 days, preferably at least 60 days, even more preferably at least 90 days, while maintained at a temperature between about 15° C. and about 25° C., preferably about 18° C. and about 24° C. In certain aspects, the peroxylactic acid in the aqueous equilibrium peroxylactic acid solution exhibits less than 10% degradation over a period of at least 30 days, preferably at least 45 days, preferably at least 60 days, even more preferably at least 90 days, while maintained at a temperature between about 15° C. and about 25° C., preferably about 18° C. and about 24° C.

In some aspects, the lactic acid added with the deionzed water is high-grade, commercially available DL-lactic acid (88% USP/FCC, CAS Number 50-21-5, 7732-18-5). In some aspects, lactic acid (88% USP/FCC) is added with the deionized water in an amount of about 22.5 to about 33.7 solution weight percent, more preferably about 23.9 to about 32.3 solution weight percent, more preferably about 25.3 to about 31.0 solution weight percent, and even more preferably about 26.7 to about 29.5 solution weight percent, of the total weight percent of the starting formulation. One of ordinary skill in the art will appreciate that the foregoing lactic acid solution weight percents will be adjusted depending upon the concentration of the lactic acid solution (e.g., 85% compared to 88%). Accordingly, the amount of lactic acid added with the deionized water, after adjusting for water in the lactic acid solution, is preferably in an amount of about 19.8 to about 29.6 weight percent, more preferably about 21.0 to about 28.4 weight percent, more preferably about 22.2 to about 27.2 weight percent, and even more preferably about 23.5 to about 25.9 weight percent, of the total weight percent of the starting formulation.

In some aspects, the amount of deionized water is a quantity sufficient for the starting formulation, which in some aspects is about 5 to about 15 weight percent, preferably about 6 to about 12 weight percent, more preferably about 7 to about 10 weight percent, of the total weight percent of the starting formulation.

In some aspects, the hydrogen peroxide added is high-grade, commercially available hydrogen peroxide (70% USP/FCC). In some aspects, the hydrogen peroxide (70%) is added in an amount of about 48.0 to about 72.0 weight percent, more preferably about 51.0 to about 69.0 weight percent, more preferably about 54.0 to about 66.6 weight percent, and even more preferably about 57.0 to about 63.0 weight percent, of the total weight percent of the starting formula composition. One of ordinary skill in the art will appreciate that the foregoing hydrogen peroxide solution weight percents will be adjusted depending upon the concentration of the hydrogen peroxide solution (e.g., 70% compared to 55%). Accordingly, the amount of hydrogen peroxide added to the blend of lactic acid and deionized water is preferably between about 33.6 to about 50.4 weight percent, more preferably about 35.7 to about 48.3 weight percent, more preferably about 37.8 to about 46.2 weight percent, and even more preferably about 39.9 to about 44.1 weight percent, of the total weight percent of the starting formulation.

When used during the process, the one or more optional sequestering agents is a high-grade, commercially available sequestering agent. In some aspects, the one or more optional sequestering agents comprises etidronic (HEDP) acid (1-Hydroxyethylidene-1,1-diphosphonic acid), ATMPT (Aminotris(methylenephosphonic acid), EDTMP (Ethylenediaminetetra(methylenephosphonic acid), TDTMP (Tetramethylenediaminetetra(methylenephosphonic acid), HDTMP (Hexamethylenediaminetetra(methylenephosphonic acid), DTPMP (Diethylenetriaminepenta(methylenephosphonic acid), 2-phosphonobutane 1,2,4-tricarboxylic acid, Nitrilotrimethylenetris (diphosphonic acid), dipicolinic acid, or mixtures thereof.

In some aspects, the one or more optional sequestering agents is added in an amount from greater than 0 up to 8.0 weight percent, more preferably greater than about 0.01 up to about 4.0 weight percent, preferably greater than about 0.02 up to about 2.0 weight percent, preferably greater than about 0.03 up to about 1.0 weight percent, more preferably greater than about 0.04 up to about 0.5 weight percent, even more preferably greater than about 0.05 up to about 0.15 weight percent, of the total weight percent.

In some aspects, the one or more optional sequestering agents comprises high-grade, commercially available HEDP (60% USP/FCC). In some aspects, HEDP is added in an amount from greater than 0 up to 0.2 weight percent, more preferably greater than about 0.01 up to about 0.175 weight percent, even more preferably greater than about 0.02 up to about 0.15 weight percent, of the total weight percent of the starting formula composition.

When used during the process, the one or more optional acid catalysts comprises one or more high-grade, commercially available inorganic acid to drive the components to the equilibrium peroxylactic acid composition. In some aspects, the one or more inorganic acid comprises phosphoric acid, sulfuric acid, sulfamic acid, hydrochloric acid, nitric acid, boric acid, or mixtures thereof. In some other aspects, the one or more inorganic acid comprises phosphoric acid. In some other aspects, the one or more inorganic acid comprises sulfuric acid. In some other aspects, the one or more inorganic acid comprises a mixture of phosphoric acid and sulfuric acid.

In some aspects, the one or more optional inorganic acids is added in an amount from greater than 0 up to about 10.0 weight percent, more preferably greater than 0.05 up to about 5.0 weight percent, more preferably greater than about 0.1 up to about 4.0 weight percent, more preferably greater than about 0.2 up to about 3.5 weight percent, and even more preferably greater than about 0.25 up to about 3.4 weight percent, of the total weight percent of the starting formulation.

In some aspects, the one or more optional inorganic acid comprises phosphoric acid added in an amount from greater than 0 up to about 10.0 weight percent, more preferably greater than 0.05 up to about 5.0 weight percent, more preferably greater than about 0.1 up to about 2.5 weight percent, more preferably greater than about 0.2 up to about 2.25 weight percent, and even more preferably greater than about 0.25 up to about 2.0 weight percent, of the total weight percent of the starting formulation.

In some aspects, the one or more optional inorganic acid comprises sulfuric acid added in an amount from greater than 0 up to about 10.0 weight percent, more preferably greater than 0.05 up to about 5.0 weight percent, more preferably greater than about 0.1 up to about 2.5 weight percent, more preferably greater than about 0.2 up to about 2.25 weight percent, and even more preferably greater than about 0.25 up to about 2.0 weight percent, of the total weight percent of the starting formulation.

In some aspects, the one or more optional inorganic acid comprises a mixture of phosphoric acid and sulfuric acid in an amount greater than 0 up to about 10.0 weight percent, more preferably greater than 0.05 up to about 5.0 weight percent, more preferably greater than about 0.1 up to about 4.0 weight percent, more preferably greater than about 0.2 up to about 3.5 weight percent, and even more preferably greater than about 0.25 up to about 3.4 weight percent, of the total weight percent of the starting formulation.

The equilibrium peroxylactic acid composition can be used for various food product applications, including soaking, dipping, chilling, spraying, quenching, rinsing and/or washing processes of a protein food product, such as red meat, poultry, pork, fish, eggs, seafood and nuts.

In some aspects, the aqueous equilibrium peroxylactic acid solution of the present invention can be diluted with a source of water to provide a peroxylactic acid use solution having a concentration of the peroxylactic acid between about 5 ppm and about 2000 ppm. In some aspects, the diluted aqueous equilibrium peroxylactic acid solution preferably has a concentration up to about 1500 ppm, in some aspects up to about 1000 ppm, in some aspects up to about 500 ppm, in some aspects up to about 250 ppm, in some aspects up to about 100 ppm, in some other aspects up to about 75 ppm, and in some aspects up to about 50 ppm.

The aqueous equilibrium peroxylactic acid solution is preferably applied to a food product at a concentration of the peroxylactic acid between about 5 ppm and about 2000 ppm. In some aspects, the aqueous equilibrium peroxylactic acid solution is preferably applied to a food product at a concentration up to about 1500 ppm, in some aspects up to about 1000 ppm, in some aspects up to about 500 ppm, in some aspects up to about 250 ppm, in some aspects up to about 100 ppm, in some other aspects up to about 75 ppm, and in some aspects up to about 50 ppm.

In some aspects, the aqueous equilibrium peroxylactic acid solution is applied to a food product at a concentration of the peroxylactic acid between about 5 ppm and about 2000 ppm, in some aspects between about 10 ppm and about 1500 ppm, in some aspects between about 20 ppm and about 1000 ppm, in some aspects between about 25 ppm and about 500 ppm, and in some other aspects between about 30 ppm and about 100 ppm.

In some aspects, the diluted peroxylactic acid use solution having a concentration up to about 2000 pm applied to a food product completely degrades to water and lactic acid within about 1 hour of contact, such that no detectable limit of peroxylactic acid or hydrogen peroxide is available after about 1 hour. In some aspects, the diluted peroxylactic acid use solution having a concentration up to about 2000 pm applied to a food product has a detectable limit of peroxylactic acid and/or hydrogen peroxide on the surface of the food product after about 30 minutes, in some aspects about 35 minutes, and in some other aspects about 40 minutes, but no detectable limit of peroxylactic acid and/or hydrogen peroxide on the surface of the food product after about 1 hour of contact.

The aqueous equilibrium peroxylactic acid solution produced by the process of the present invention contains peroxylactic acid present in an amount of about 2.5 to about 15.0 weight percent, preferably about 5.0 to about 12.5 weight percent, preferably about 9.0 to about 11.5 weight percent, more preferably about 9.5 to about 11.0 weight percent, of the total weight percent of the equilibrium peroxylactic acid solution.

The amount of hydrogen peroxide in the aqueous equilibrium peroxylactic acid solution produced by the present invention is about 19.0 to about 30.0 weight percent, preferably about 20.5 to about 28.0 weight percent, preferably about 22.0 to about 27.0 weight percent, more preferably about 23.0 to about 25.5 weight percent, of the total weight percent of the equilibrium peroxylactic acid solution.

The amount of lactic acid in the aqueous equilibrium peroxylactic acid solution produced by the process of the present invention is about 1.0 to about 10.0 weight percent, preferably about 2.0 to about 5.0 weight percent, preferably about 2.5 to about 4.5 weight percent, more preferably about 3.0 to about 4.0 weight percent, of the total weight percent of the equilibrium peroxylactic acid solution.

When the one or more optional sequestering agents is used to produce the aqueous equilibrium peroxylactic acid solution by the present invention, the aqueous equilibrium peroxylactic acid solution contains the one or more sequestering agents is present in an amount from greater than 0 up to 0.1 weight percent, more preferably greater than about 0.02 up to about 0.08 weight percent, even more preferably greater than about 0.03 up to about 0.075 weight percent, of the total weight percent of the equilibrium peroxylactic acid solution.

When the one or more optional acid catalysts is used to produce the aqueous equilibrium peroxylactic acid solution by the present invention, the aqueous equilibrium peroxylactic acid solution contains the one or more optional acid catalysts in an amount greater than 0 up to about 8.0 weight percent, more preferably greater than about 0.1 up to about 4.0 weight percent, more preferably greater than about 0.25 up to about 3.75 weight percent, and even more preferably greater than about 0.3 up to about 3.5 weight percent, of the total weight percent of the equilibrium peroxylactic acid solution.

The aqueous equilibrium peroxylactic acid solution produced by the process of any preceding claim, wherein the aqueous equilibrium peroxylactic acid solution has a pH greater than 0.5 and less than about 3.0, preferably less than about 2.75, preferably less than about 2.5, preferably less than about 2.25, preferably less than about 2.0, preferably less than about 1.75, preferably less than about 1.5, preferably less than about 1.25, preferably less than about 1.0, and in some aspects preferably less than about 0.75.

In some aspects, the aqueous equilibrium peroxylactic acid solution can be pH modified to lower the pH or to raise the pH. In some aspects, the pH of the aqueous equilibrium peroxylactic acid solution is lowered using an alkali agent. In some aspects, the pH of the aqueous equilibrium peroxylactic acid solution can be lowered to a pH range of about 0.5 to about 4.0, in some aspects between about 0.75 and about 3.0, and in some other aspects between about 1.0 and about 2.0. In some aspects, the pH of the aqueous equilibrium peroxylactic acid solution is raised using an alkaline agent. In some aspects, the pH of the aqueous equilibrium peroxylactic acid solution can be raised above about 6.0, in some aspect up to about 7.0, in some aspect up to about 8.0, in some aspect up to about 9.0, and in some other aspects in some aspect up to about 10.0 using an alkaline agent. In some aspects, the pH of the aqueous equilibrium peroxylactic acid solution can be raised to a pH range of about 6.8 to about 10.0, in some aspects between about 7.0 and about 9.0, and in some other aspects between about 7.5 and about 8.5.

The pH modified peroxylactic acid can be prepared by combining the aqueous equilibrium peroxylactic acid solution of the present invention with one or more buffering agents chosen from sodium hydroxide, potassium hydroxide, the sodium salt of carbonic acid, the potassium salt of carbonic acid, phosphoric acid, silicic acid or mixtures thereof, in a quantity that is necessary to bring the solution to the desired pH or pH range. One of ordinary skill in the art will appreciate that other alkali and alkalizing chemistries approved for direct food contact may also be used, whether alone or in combination with any of the foregoing buffering agents. The quantity of the buffering agent in a buffered peroxycarboxylic acid solution will generally be in the range of about 0.01% to about 10% by volume of the total solution, but other volumes of the buffering agent may be utilized depending upon various parameters, such as local water condition, including pH, hardness and conductivity.

A representative embodiment of the components to manufacture the aqueous equilibrium peroxylactic acidic composition of the present invention is shown in Table 1.

TABLE 1

Representative Manufacturing Formula.

| Component | % Weight |
| --- | --- |
| Water | q.s. (~0.0-46.6) |
| Lactic Acid | 19.8-29.7 |
| HEDP (optional) | 0-4.8 |
| Sulfuric Acid (optional) | 0-9.5 |
| Phosphoric Acid (optional) | 0-7.5 |
| Hydrogen Peroxide | 33.6-50.4 |

A representative embodiment of the components of a resulting aqueous equilibrium peroxylactic acidic composition manufactured from the components shown in Table 1 is provided in Table 2, where the quantity of water is to balance the solution to a 100% solution with a quantity sufficient.

TABLE 2

Resulting Aqueous Equilibrium Product.

| Component | % w/w |
| --- | --- |
| Water | q.s. (~28.9-77.5) |
| Peroxylactic Acid | 2.5-15.0 |
| Lactic Acid | 1.0-10.0 |
| Hydrogen Peroxide | 19.0-30.0 |
| HEDP (optional) | 0-0.1 |
| Sulfuric Acid (optional) | 0.-8.0 |
| Phosphoric Acid (optional) | 0-8.0 |

A presently preferred representative embodiment of the components to manufacture the aqueous equilibrium peroxylactic acidic composition of the present invention using a sequestering agent and inorganic acid catalysts is shown in Table 3.

TABLE 3

Representative Manufacturing Formula.

| Component | % Weight |
| --- | --- |
| Water | q.s. (~26.06-36.15) |
| Lactic Acid | 23.5-26.0 |
| HEDP (optional) | 0.03-0.09 |
| Sulfuric Acid (optional) | 0.24-2.0 |
| Phosphoric Acid (optional) | 0.18-1.75 |
| Hydrogen Peroxide | 39.9-44.1 |

A representative embodiment of the components of the resulting aqueous equilibrium peroxylactic acidic composition manufactured from the components shown in Table 3 is provided in Table 4.

TABLE 4

Resulting Aqueous Equilibrium Product.

| Component | % w/w |
| --- | --- |
| Water | q.s. (~49.425-69.27) |
| Peroxylactic Acid | 8.1-11.0 |
| Lactic Acid | 3.0-4.0 |
| Hydrogen Peroxide | 19.0-28.5 |
| HEDP (optional) | 0.03-0.075 |
| Sulfuric Acid (optional) | 0.3-3.5 |
| Phosphoric Acid (optional) | 0.3-3.5 |

The aqueous equilibrium peroxylactic acid compositions of the present invention can be used as antimicrobial use solutions in soaking, dipping, chilling, spraying, quenching, rinsing and/or washing processes of a food product, such as red meat, poultry, pork, fish, eggs, seafood and nuts. In some aspects, the aqueous equilibrium peroxylactic acid compositions of the present invention can used as antimicrobial use solutions to reduce pathogens on such food products, including at least *E. coli* O157:H7 and other Shiga toxin-producing *E. coli* (STECs), *Salmonella*, *Campylobacter*, and *Listeria*.

In some aspects, the aqueous equilibrium peroxylactic acid compositions of the present invention can used as antimicrobial use solutions to reduce pathogens by $\log_{10}$ reduction of at least 0.5, in some aspects at least 0.6, in some aspects at least 0.75, in some aspects at least 1.0, in some other aspects at least 1.5.

In some aspects, the aqueous equilibrium peroxylactic acid compositions of the present invention can have a $\log_{10}$ reduction of at least 0.35, in some aspects at least 0.40, in some aspects at least 0.45, greater than a comparable aqueous equilibrium peroxyacetic acid composition applied using the same technique for the same period of time at the same concentration.

EXAMPLES

Example 1—Equilibrium Peroxylactic Acid Formation

The components in Table 5 were added to a clean, dry mixing vessel by weight in the order in which they are listed.

TABLE 5

Manufacturing Formula Components.

| Component | % Weight |
| --- | --- |
| Deionized Water | q.s. (~29.84) |
| Lactic Acid | 24.7 |
| HEDP | 0.06 |
| Sulfuric Acid | 1.9 |
| Phosphoric Acid | 1.5 |
| Hydrogen Peroxide | 42.0 |

After blending the lactic acid with the deionized water, the mixer was turned on to allow the batch to agitate during the remainder of the component additions, and for about 3 to about 6 hours after the last component was added. With continued mixing, the mixture was temperature controlled at a temperature above about 45° C. and below about 55° C. for a period of 5 days to allow the mixture to establish equilibrium. Titration was used to determine the solution in the equilibrium state, and then the aqueous equilibrium peroxylactic acid solution was placed in a container and stored at a temperature of between about 18° C. and about 24° C. The resulting aqueous equilibrium peroxylactic acid solution contained the components shown in Table 6.

TABLE 6

Aqueous Equilibrium Peroxylactic Acid Solution Components.

| Component | % w/w |
| --- | --- |
| Water | q.s. (~58.36) |
| Peroxylactic Acid | 10.18 |
| Lactic Acid | 3.73 |
| Hydrogen Peroxide | 24.27 |
| HEDP (optional) | 0.06 |
| Sulfuric Acid (optional) | 1.9 |
| Phosphoric Acid (optional) | 1.5 |

Example 2—Storage Stability of Equilibrium Peroxylactic Acid Solution

An equilibrium peroxylactic acid solution was formed using the same process and components described in Example 1, except maintaining the mixture at a temperature above about 45° C. and below about 55° C. occurred for a period of 4 days. Upon reaching the equilibrium state, the aqueous equilibrium peroxylactic acid solution was tested to determine the stability of the hydrogen peroxide and peroxylactic acid content over a period of time. The stability of the hydrogen peroxide and peroxylactic acid content was determined by titration measuring each of the hydrogen peroxide and peroxylactic acid content in the aqueous equilibrium peroxylactic acid solution, as shown in Table 7.

TABLE 7

Stability of Aqueous Equilibrium Peroxylactic Acid Solution.

| PLA Solution - Days | % $H_2O_2$ (w/w) | % PLA (w/w) |
| --- | --- | --- |
| 0 | 24.86 | 9.20 |
| 7 | 27.34 | 10.03 |
| 14 | 27.63 | 9.98 |
| 30 | 23.67 | 10.40 |
| 60 | 22.74 | 10.29 |
| 90 | 21.50 | 9.80 |

As shown in Table 7, the hydrogen peroxide and peroxylactic acid content in the aqueous equilibrium peroxylactic acid solution remained relatively stable over a period of 60 days with less than a 10% degradation over the 60 days and less for each component. As it relates to 90 days, there was less than a 15% degradation of hydrogen peroxide and less than a 10% degradation of peroxylactic acid.

Without wishing to be bound by theory, it is believed that the increase in the hydrogen peroxide and peroxylactic acid content between the day 0 and day 90 period of time was due to continued equilibrium shifts of the components in the solution as some degradation and regeneration of components occurred with the curing at a temperature above about 45° C. and below about 55° C. being stopped after 4 days. As one of ordinary skill in the art will appreciate, an aqueous equilibrium peroxylactic acid solution is not a static situation, such that the % w/w of each component has some fluctuation over time in the equilibrium state before the peroxylactic acid and hydrogen peroxide components degrade into lactic acid, water and oxygen gas. The equilibrium peroxylactic acid solution of the present invention will generally comprise about 2.5 to about 15.0 weight percent peroxylactic acid and about 19.0 and about 30.0 weight percent hydrogen peroxide, more preferably about 8.1 and about 11.0 weight percent peroxylactic acid and about 21.0 and about 28.5 hydrogen peroxide.

Example 3—Degradation Profile on Protein Sources

The degradation profile of the equilibrium peroxylactic acid solution was compared to the degradation time of a comparable equilibrium peroxyacetic acid solution upon contact with a poultry protein source over the dwell times of 0, 15, 30, 45, 60, 90 and 120 minutes at 4° C. A 2000 ppm aqueous equilibrium peroxylactic acid solution was prepared from the aqueous equilibrium peroxylactic acid solution formed in Example 1. For each dwell time, five separate 200 mL aliquots of the 2000 ppm aqueous equilibrium peroxylactic acid solution were each distributed into a separate Ziploc bag, with the weight of each bag being having the 200 mL aliquot being obtained, such that each dwell time had five test results. A comparative 2000 ppm aqueous equilibrium peroxyacetic acid solution was also prepared. For each dwell time, five separate 200 mL aliquots of the 2000 ppm aqueous equilibrium peroxyacetic acid solution were each distributed into a separate Ziploc bag, with the weight of each bag having the 200 mL aliquot being obtained, such that each dwell time had five test results. For each of the five test results for each use solution applied to the poultry protein sample at the respective dwell times, a 200 mL aliquot of deionized water in a Ziploc bag was also prepared (e.g., 70 in total).

For the five tests at each dwell time (0, 15, 30, 45, 60, 90 and 120 minutes), one chicken breast was placed into one bag containing the 200 mL aliquot of 2000 ppm aqueous equilibrium peroxylactic acid solution and the contents gently shaken at 4° C. to simulate immersion in a dip tank in a poultry processing plant. For the 0 minute dwell time, the contents were shaken for 45 seconds at 4° C. After each sample reached its dwell time, the chicken breast was removed from the bag and allowed to drip for 15 seconds. Each bag was weighed after chicken breast removal to determine the aqueous equilibrium peroxylactic acid solution on the chicken breast surface. After dripping for 15 seconds, each chick breast was placed into a fresh bag having the 200 mL aliquot of deionized water and shaken gently for 45 seconds to release the aqueous equilibrium peroxylactic acid solution from the chicken breast surface. The chicken breast was then removed from the deionized water and a sample of the water was immediately obtained and titrated to determine the concentration of peroxylactic acid and hydrogen peroxide present. Each dwell time had five test results relating to the poultry protein source being chicken breast.

For the comparative aqueous equilibrium peroxylactic acid use solution, the same steps were performed for the chicken breasts placed into the aliquots for each dwell time, such that each dwell time for the comparative aqueous equilibrium peroxylactic acid use solution also had five test results. The water sample was also immediately obtained and titrated to determine the concentration of peroxyacetic acid and hydrogen peroxide present.

The average concentration of peroxylactic acid/peroxyacetic acid and hydrogen peroxide present for the five test results at each dwell time on the poultry protein source is provided in Table 8.

TABLE 8

Degradation Profile of Use Solutions for Poultry Protein Source.

| | PAA | | PLA | |
|---|---|---|---|---|
| Time (min) | $H_2O_2$ ppm | PAA ppm | $H_2O_2$ ppm | PLA ppm |
| 0 | 182 | 2000 | 3606 | 2000 |
| 15 | 15 | 122 | 273 | 545 |
| 30 | 0 | 26 | 61 | 182 |
| 45 | 0 | 0 | 0 | 10 |
| 60 | 0 | 0 | 0 | 0 |
| 90 | 0 | 0 | 0 | 0 |
| 120 | 0 | 0 | 0 | 0 |

The degradation profile of the equilibrium peroxylactic acid solution was also compared to the degradation time of a comparable equilibrium peroxyacetic acid solution upon contact with a beef protein source over the dwell times of 0, 15, 30, 45, 60, 90 and 120 minutes at 4° C. Five test results were obtained at each dwell time for both the 2000 ppm aqueous equilibrium peroxylactic acid solution and the 2000 ppm aqueous equilibrium peroxyacetic acid solution using the same methodology and steps for the poultry protein source, except using a beef eye of round cut of about 250 grams for the beef protein source.

The average concentration of peroxylactic acid/peroxyacetic acid and hydrogen peroxide present for the five test results at each dwell time on the beef protein source is provided in Table 9.

TABLE 9

Degradation Profile of Use Solutions for Beef Protein Source.

| | PAA | | PLA | |
|---|---|---|---|---|
| Time (min) | $H_2O_2$ ppm | PAA ppm | $H_2O_2$ ppm | PLA ppm |
| 0 | 283 | 2000 | 3826 | 2000 |
| 15 | 22 | 75 | 174 | 261 |
| 30 | 0 | 15 | 76 | 130 |
| 45 | 0 | 0 | 0 | 18 |
| 60 | 0 | 0 | 0 | 0 |
| 90 | 0 | 0 | 0 | 0 |
| 120 | 0 | 0 | 0 | 0 |

As shown in Tables 8 and 9, the aqueous equilibrium peroxylactic acid solution used as an antimicrobial solution on the surface of exposed meat and poultry products was observed to degrade completely within 1 hour of contact. The constituent degradation products of the aqueous equilibrium peroxylactic acid solution being lactic acid, water and oxygen. The aqueous equilibrium peroxylactic acid use solution degrades slightly slower up to about 40 minutes than a comparable aqueous equilibrium peroxyacetic acid use solution, but then rapidly catches up to peroxyacetic acid level of degradation as time progresses to 60 minutes. The increased stability of aqueous equilibrium peroxylactic acid use solutions is desirable, requiring the use of less chemistry to achieve the same desired effect as compared to aqueous equilibrium peroxyacetic acid use solutions, and less make-up chemistry as the use solutions are depleted during food processing and make-up water addition that is required to maintain acceptable levels in dip tank applications.

Example 4—Antimicrobial Efficacy on Beef Via Spray Application

The antimicrobial efficacy the equilibrium peroxylactic acid solution was determined by preparing a 1000 ppm aqueous equilibrium peroxylactic acid use solution from the aqueous equilibrium peroxylactic acid solution formed in Example 1. The 1000 ppm aqueous equilibrium peroxylactic acid use solution was tested on five samples of beef cubes having approximately 100 cm$^2$ surface area that had been incubated for about 2 hours in 1000 mL of Nutrient Broth containing *E. coli* O157:H7 that had grown to a concentration of $\geq 10^6$. The beef cube samples had been removed from the broth and allowed to air dry for 15 to 30 minutes at room temperature prior to the 1000 ppm aqueous equilibrium peroxylactic acid use solution being applied. For the spray application of the 1000 ppm aqueous equilibrium peroxylactic acid use solution, each beef cube substrate was suspended and sprayed until dripping wet. After allowing each beef cube substrate drip for 15 seconds, each beef cube substrate was vigorously shaken for 45 seconds in a Ziploc bag containing 200 mL of neutralizing buffered peptone water pursuant to USDA's Food Safety and Inspection Service regulations updated Nov. 1, 2017 (FSIS nBPW—20.g of buffered peptone, 7 g of refined soy lecithin or equivalent, 1 g of sodium thiosulfate, 1 L of microbiologically suitable water, and 12.5 g of sodium bicarbonate). A 100 µL sample from each nBPW solution bag was removed and injected into 9.9 mL of sterile phosphate buffer solution to create a 10' dilution, which was serially diluted to $10^{-5}$, plated on MacConkey Agar, and incubated for 24 hours. Two controls were also used by following the same steps of treating each beef cube substrate after incubating in the broth, except the beef cube substrates were sprayed with deionized water instead of use solution prior to being allowed to drip and placed in a bag having the FSIS nBPW. The average reductions were obtained by subtracting the individual plate results from the Control $\log_{10}$ average, and then averaging. The test of 5 replicates and 2 controls was run three times to get an average $\log_{10}$ reduction, as shown from the data in Table 10.

TABLE 10

Antimicrobial $\log_{10}$ Reduction of 1000 PLA at 15 seconds against *E. Coli* O157:H7 on Beef via Spray Application.

| TEST 1 | | | |
|---|---|---|---|
| Controls CFU count | Total Count w dilution factor | Control Average | Control Avg log 10 |
| 174 | 1.74E+06 | — | — |
| 280 | 2.80E+06 | — | — |

TABLE 10-continued

Antimicrobial $\log_{10}$ Reduction of 1000 PLA at 15 seconds against *E. Coli* O157:H7 on Beef via Spray Application.

| | | | 2.27E+06 | 6.36 |
|---|---|---|---|---|
| CFU count | Total Count w dilution factor | log10 | log10 reduction | Avg log10 reduction |
| 36 | 3.60E+04 | 4.56 | 1.80 | — |
| 64 | 6.40E+04 | 4.81 | 1.55 | — |
| 32 | 3.20E+04 | 4.51 | 1.85 | — |
| 48 | 4.80E+04 | 4.68 | 1.67 | — |
| 24 | 2.40E+04 | 4.38 | 1.98 | — |
| | | | | 1.77 |

| TEST 2 | | | |
|---|---|---|---|
| Controls CFU count | Total Count w dilution factor | Control Average | Control Avg log 10 |
| 64 | 6.40E+05 | — | — |
| 53 | 5.30E+05 | — | — |
| | | 5.85E+05 | 5.77 |

| CFU count | Total Count w dilution factor | log10 | log10 reduction | Avg log10 reduction |
|---|---|---|---|---|
| 91 | 9.10E+03 | 3.96 | 1.81 | — |
| 29 | 2.90E+04 | 4.46 | 1.30 | — |
| 249 | 2.49E+04 | 4.40 | 1.37 | — |
| 161 | 1.61E+04 | 4.21 | 1.56 | — |
| 167 | 1.67E+04 | 4.22 | 1.54 | — |
| | | | | 1.52 |

| TEST 3 | | | |
|---|---|---|---|
| Controls CFU count | Total Count w dilution factor | Control Average | Control Avg log 10 |
| 24 | 2.40E+05 | — | — |
| 57 | 5.70E+05 | — | — |
| | | 4.05E+05 | 5.61 |

| CFU count | Total Count w dilution factor | log10 | log10 reduction | Avg log10 reduction |
|---|---|---|---|---|
| 211 | 2.11E+04 | 4.32 | 1.28 | — |
| 175 | 1.75E+04 | 4.24 | 1.36 | — |
| 133 | 1.33E+04 | 4.12 | 1.48 | — |
| 114 | 1.14E+04 | 4.06 | 1.55 | — |
| 154 | 1.54E+04 | 4.19 | 1.42 | — |
| | | | | 1.42 |
| | | 3 Test Average: | | 1.57 |

The results of this testing illustrate that aqueous equilibrium peroxylactic acid use solutions are an effective antimicrobial against *E. coli*. Considering the rigorous parameters of this testing, it is contemplated that aqueous equilibrium peroxylactic acid use solutions will perform well at 1000 ppm and 10 s contact time in reducing *E. coli*/Shiga toxin-producing *E. coli* pathogens on meat products in processing plants.

Example 5—Antimicrobial Efficacy on Poultry Via Dip Application

The antimicrobial efficacy the equilibrium peroxylactic acid solution was determined by preparing a 10 ppm aqueous equilibrium peroxylactic acid use solution from the aqueous equilibrium peroxylactic acid solution formed in Example 1. The 10 ppm aqueous equilibrium peroxylactic acid use solution was tested on five samples of chicken legs having approximately 100 cm$^2$ surface area that had been incubated for about 2 hours in 1000 mL of Nutrient Broth containing *Salmonella enteric* serovar *Infantis* (SI) that had grown to a concentration of ≥10⁶. The chicken leg samples had been removed from the broth and allowed to air dry for 15 to 30 minutes at room temperature prior to the 10 ppm aqueous equilibrium peroxylactic acid use solution being applied. For the dip application of the 10 ppm aqueous equilibrium peroxylactic acid use solution, each chicken leg was placed in a Ziploc bag containing 200 mL of the 10 ppm use solution and agitated for about 1 hour on a platform shaker. After each chicken leg substrate was removed from the bag and allowed to drip for 15 seconds, each chicken leg substrate was vigorously shaken for 45 seconds in a Ziploc bag containing 200 mL of FSIS nBPW. A 100 µL sample from each nBPW solution bag was removed and injected into 9.9 mL of sterile phosphate buffer solution to create a 10' dilution, which was serially diluted to $10^{-5}$, plated on *Salmonella-Shigella* Agar, and incubated for 24 hours at 35° C. Two controls were also used by following the same steps of treating each chicken leg after being incubated in the broth, except the chicken leg substrates were agitated in a bag having the FSIS nBPW instead of the use solution. The average reductions were obtained by subtracting the individual plate results from the Control $\log_{10}$ average, and then averaging. The test of 5 replicates and 2 controls was run three times to get an average $\log_{10}$ reduction, as shown from the data in Table 11.

TABLE 11

Antimicrobial $\log_{10}$ Reduction of 10 PLA at 1 hour against *Salmonella Enteric serovar Infantis* on Poultry via Dip Application.

| TEST 1 | | | |
|---|---|---|---|
| Controls CFU count | Total Count w dilution factor | Control Average | Control Avg log 10 |
| 29 | 2.90E+04 | — | — |
| 42 | 4.20E+04 | — | — |
| | | 3.55E+04 | 4.55 |

| CFU count | Total Count w dilution factor | log10 | log10 reduction | Avg log10 reduction |
|---|---|---|---|---|
| 149 | 1.49E+04 | 4.17 | 0.38 | — |
| 51 | 5.10E+03 | 3.71 | 0.84 | — |
| 56 | 5.60E+03 | 3.75 | 0.80 | — |
| 40 | 4.00E+03 | 3.60 | 0.95 | — |
| 24 | 2.40E+03 | 3.38 | 1.17 | — |
| | | | | 0.83 |

| TEST 2 | | | |
|---|---|---|---|
| Controls CFU count | Total Count w dilution factor | Control Average | Control Avg log 10 |
| 280 | 2.80E+04 | — | — |
| 308 | 3.08E+04 | — | — |
| | | 2.94E+04 | 4.47 |

| CFU count | Total Count w dilution factor | log10 | log10 reduction | Avg log10 reduction |
|---|---|---|---|---|
| 51 | 5.10E+03 | 3.71 | 0.76 | — |
| 120 | 1.20E+04 | 4.08 | 0.39 | — |
| 45 | 4.50E+03 | 3.65 | 0.82 | — |
| 81 | 8.10E+03 | 3.91 | 0.56 | — |
| 77 | 7.70E+03 | 3.89 | 0.58 | — |
| | | | | 0.62 |

TABLE 11-continued

Antimicrobial $\log_{10}$ Reduction of 10 PLA at 1 hour against *Salmonella Enteric serovar Infantis* on Poultry via Dip Application.

| TEST 3 | | | |
|---|---|---|---|
| Controls CFU count | Total Count w dilution factor | Control Average | Control Avg log 10 |
| 34 | 3.40E+04 | — | — |
| 27 | 2.70E+04 | — | — |
| | | 3.05E+04 | 4.48 |

| CFU count | Total Count w dilution factor | log10 | log10 reduction | Avg log10 reduction |
|---|---|---|---|---|
| 81 | 8.10E+03 | 3.91 | 0.58 | — |
| 64 | 6.40E+03 | 3.81 | 0.68 | — |
| 83 | 8.30E+03 | 3.92 | 0.57 | — |
| 22 | 2.20E+03 | 3.34 | 1.14 | — |
| 47 | 4.70E+03 | 3.67 | 0.81 | — |
| | | | | 0.75 |
| | | 3 Test Average: | | 0.73 |

The results of these three tests indicate that, even at 10 ppm, PLA exposure for 1 hour in a dip application significantly reduces SI on chicken.

Example 6—Comparative Antimicrobial Efficacy on Beef and Poultry Substrates

The antimicrobial efficacy of a 400 ppm aqueous equilibrium peroxylactic acid solution prepared from the solution formed in Example 1 was compared to a 400 ppm aqueous equilibrium peroxyacetic acid solution on both beef and poultry substrates against *Salmonella enterica* serovar *enteriditis* via dip application for 15 seconds. This dilution of 400 ppm is near the middle of a commonly used range of about 200-800 ppm for many spray and dip applications in both meat and poultry processing plants. Depending on application and contact time available, more or less concentrated antimicrobial solutions may be used for a particular application. As well as available contact time, other factors, like cost, safety, solution temperature, and number of intervention sites used, factor into the selection of use concentration. The intended technical effect for antimicrobial intervention chemistries is always to maximize the additive antimicrobial effect of all of the intervention sites to aid in protecting food safety.

Each of the 400 ppm use solutions (PLA and PAA) were tested on ten samples of beef cubes and ten samples of chicken legs, having approximately 100 cm² surface area that had been incubated for about 2 hours in 1000 mL of Nutrient Broth containing *Salmonella enterica* serovar *enteriditis* that had grown to a concentration of ≥10⁶. Each substrate (beef cube or chicken leg) had been removed from the broth and allowed to air dry for 15 to 30 minutes at room temperature prior to the respective 400 ppm use solution being applied by dip application. For the dip application, each substrate was placed in a Ziploc bag containing 200 mL of the respective 400 ppm use solution and agitated for about 15 seconds. After each substrate was removed from the bag and allowed to drip for 15 seconds, each substrate was vigorously shaken for 45 seconds in a Ziploc bag containing 200 mL of a lecithin/sodium thiosulfate neutralizing medium (LST). A 100 µL sample from each LST solution bag was removed and injected into 9.9 mL of sterile phosphate buffer solution to create a 10' dilution, which was serially diluted to $10^{-5}$, plated on *Salmonella-Shigella* Agar, and incubated for 24 hours at 35° C. Two sets of controls were used, with each control set having two control replicates, by following the same steps of treating each substrate after being incubated in the broth, except the substrates were agitated in a bag having LST instead of the respective use solution. The average reductions were obtained by subtracting the individual plate results from the respective Control $\log_{10}$ average, and then averaging. Test results for the beef cube substrate contained 10 replicates, and the chicken leg substrate contained 10 replications, which with the respective controls is shown in the data of Table 12.

TABLE 12

Comparative Antimicrobial $\log_{10}$ Reduction of PLA and PAA.

Beef

| Control log10 Reduction | PAA log 10 Reduction | PLA log 10 Reduction |
| --- | --- | --- |
| 5.00 | 4.27 | 3.99 |
|  | 4.25 | 3.92 |
|  | 4.30 | 3.92 |
|  | 4.38 | 4.00 |
|  | 4.37 | 4.01 |
|  | 4.29 | 3.97 |
|  | 4.32 | 3.87 |
|  | 4.24 | 3.94 |
|  | 4.38 | 4.02 |
|  | 4.28 | 3.89 |
| Ave. Reduction | 0.69 | 1.05 |

Poultry

| Control log10 Reduction | PAA log 10 Reduction | PLA log 10 Reduction |
| --- | --- | --- |
| 5.66 | 4.92 | 4.61 |
|  | 4.89 | 4.58 |
|  | 5.24 | 4.65 |
|  | 4.96 | 4.62 |
|  | 4.88 | 4.52 |
|  | 4.81 | 4.51 |
|  | 5.25 | 4.54 |
|  | 4.98 | 4.62 |
|  | 4.99 | 4.53 |
|  | 5.32 | 4.65 |
| Ave. Reduction | 0.64 | 1.08 |

The results of this testing illustrate that a PLA use solution is at least as effective an antimicrobial against *Salmonella enterica* serovar *enteriditis* on both beef and poultry substrates as a comparative PAA use solution at the same concentration applied to the same substrate for the same period of time.

Various embodiments have been described herein. These embodiments are given only by way of example and are not intended to limit the scope of the claimed inventions. It should be appreciated, moreover, that the various features of the embodiments that have been described may be combined in various ways to produce numerous additional embodiments.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

The invention claimed is:

1. A process for producing a peroxylactic acid solution, the process comprising:
forming a mixture comprising lactic acid, deionized water, hydrogen peroxide, one or more optional acid catalysts, and one or more optional sequestering agents, wherein an amount of lactic acid in the mixture is between about 19.8 wt-% and about 29.7 wt-%, an amount of hydrogen peroxide in the mixture is between about 33.6 wt-% and about 50.4 wt-%, and a molar ratio of hydrogen peroxide to lactic acid in the mixture is at least 3:1 (hydrogen peroxide:lactic acid); and
maintaining a heat of the mixture for a period of time of about 24 hours to about 7 days at a temperature greater than about 30° C. and below about 100° C. to allow the mixture to react to achieve an equilibrium peroxylactic acid solution;
wherein the equilibrium peroxylactic acid solution has a pH less than about 6.0 and comprises peroxylactic acid in an amount between about 2.5% and about 15.0% (w/w), lactic acid in an amount between about 1.0% and about 10.0% (w/w) and hydrogen peroxide in an amount between about 19.0% and about 30.0% (w/w).

2. The process for producing a peroxylactic acid solution according to claim 1, further comprising the step of combining the equilibrium peroxylactic acid solution with one or more buffering agents to raise the pH above about 6.0 to provide a pH modified peroxylactic acid solution.

3. The process for producing a peroxylactic acid solution according to claim 2, wherein the one or more buffering agents are chosen from sodium hydroxide, potassium hydroxide, or mixtures thereof.

4. The process for producing a peroxylactic acid solution according to claim 3, wherein the one or more buffering agents are combined with the equilibrium peroxylactic acid solution to raise the pH above about 6.8 to about 10.0.

5. The process for producing the peroxylactic acid solution according to claim 1, further comprising combining the lactic acid with the deionized water to form a lactic acid blend, and wherein the mixture is continually mixed for at least about 30 minutes and up to about 6 hours after the hydrogen peroxide is mixed into the lactic acid blend, and wherein the heat of the mixture is maintained between about 25° C. and about 90° C. for at least a portion of the time that the mixture is continually mixed.

6. The process for producing the peroxylactic acid solution according to claim 5, wherein the step of maintaining the heat of the mixture comprises heating the mixture, cooling the mixture, allowing the mixture to stay within the desired temperature range, or a combination thereof, while the starting formula components of the mixture react to form the equilibrium peroxylactic acid solution.

7. The process for producing the peroxylactic acid solution according to claim 1, wherein the amount of lactic acid in the mixture is between about 21.0 wt-% to about 28.4 wt-%, of the total weight percent, and the amount of hydrogen peroxide in the mixture is between about 35.7 wt-% to about 48.3 wt-%, of the total weight percent.

8. The process for producing the peroxylactic acid solution according to claim 1, wherein the amount of lactic acid in the mixture is between about 22.2 wt-% to about 27.2 wt-%, of the total weight percent, and the amount of hydrogen peroxide in the mixture is between about 37.8 wt-% to about 46.2 wt-%, of the total weight percent.

9. The process for producing the peroxylactic acid solution according to claim 1, wherein the amount of lactic acid in the mixture is between about 23.5 wt-% to about 25.9 wt-%, of the total weight percent, and the amount of hydrogen peroxide in the mixture is between about 39.9 wt-% to about 44.1 wt-%, of the total weight percent.

10. The process for producing the peroxylactic acid solution according to claim 1, wherein the molar ratio of hydrogen peroxide to lactic acid in the mixture is at least 3:1 to about 6:1 (hydrogen peroxide:lactic acid).

11. The process for producing the peroxylactic acid solution according to claim 1, wherein the one or more acid catalysts are present in the mixture in an amount between about 0.05 wt-% to about 10.0 wt-% of the total weight percent.

12. The process for producing the peroxylactic acid solution according to claim 11, wherein the one or more optional acid catalysts comprises one or more inorganic acids comprising phosphoric acid, sulfuric acid, sulfamic acid, hydrochloric acid, nitric acid, boric acid, or mixtures thereof.

13. The process for producing the peroxylactic acid solution according to claim 1, wherein the one or more optional sequestering agents are present in the mixture in an amount between about 0.02 wt-% and about 8.0 wt-% of the total weight percent.

14. The process for producing the peroxylactic acid solution according to claim 13, wherein the one or more optional sequestering agents comprises etidronic (HEDP) acid (1-Hydroxyethylidene-1,1-diphosphonic acid), ATMPT (Aminotris(methylenephosphonic acid), EDTMP (Ethylenediaminetetra(methylenephosphonic acid), TDTMP (Tetramethylenediaminetetra(methylenephosphonic acid), HDTMP (Hexamethylenediaminetetra(methylenephosphonic acid), DTPMP (Diethylenetriaminepenta(methylenephosphonic acid), 2-phosphonobutane 1,2,4-tricarboxylic acid, Nitrilotrimethylenetris (diphosphonic acid), dipicolinic acid, or mixtures thereof.

15. The process for producing the peroxylactic acid solution according to claim 1, wherein the amount of lactic acid in the mixture is between about 21.0 wt-% and about 28.4 wt-%, the amount of hydrogen peroxide in the mixture is between about 35.7 wt-% and about 48.3 wt-%, the one or more acid catalysts are present in the mixture in an amount between about 0.2 wt-% and about 2.25 wt-%, and the one or more optional sequestering agents are present in the mixture in an amount between about 0.04 wt-% and about 0.5 wt-%, of the total weight percent of the mixture.

16. The process for producing the peroxylactic acid solution according to claim 15, wherein the equilibrium peroxylactic acid comprises peroxylactic acid in an amount between about 5.0% and about 12.5% (w/w), lactic acid in an amount between about 2.0% and about 5.0% (w/w), hydrogen peroxide in an amount between about 20.5% and about 28.0% (w/w), the one or more optional acid catalysts in an amount less than about 2.25% (w/w), and the one or more optional sequestering agents in an amount less than about 0.5% (w/w), of the total weight percent of the equilibrium peroxylactic acid solution.

17. The process for producing the peroxylactic acid solution according to claim 15, wherein the amount of lactic acid in the mixture is between about 22.2 wt-% and about 27.2 wt-%, the amount of hydrogen peroxide in the mixture is between about 37.8 wt-% and about 46.2 wt-%, the one or more optional acid catalysts are present in the mixture in an amount between about 0.1 wt-% and about 2.5 wt-%, and the one or more optional sequestering agents are present in the mixture in an amount between about 0.04 wt-% and about 0.5 wt-%, of the total weight percent of the mixture.

18. The process for producing the peroxylactic acid solution according to claim 17, wherein the equilibrium peroxylactic acid comprises peroxylactic acid in an amount between about 9.0% and about 11.5% (w/w), lactic acid in an amount between about 2.5% and about 4.5% (w/w), hydrogen peroxide in an amount between about 22.0% and about 27.0% (w/w), the one or more optional acid catalysts in an amount between about 0.25% and about 3.75% (w/w), and the one or more optional sequestering agents in an amount between about 0.02% and about 0.08% (w/w), of the total weight percent of the equilibrium peroxylactic acid solution.

19. The process for producing the peroxylactic acid solution according to claim 1, wherein the one or more optional sequestering agents, the one or more optional acid catalysts, and the hydrogen peroxide are added sequentially to a blend of the lactic acid and deionized water.

20. The process for producing the peroxylactic acid solution according to claim 1, further comprising the step of lowering the temperature and maintaining the equilibrium peroxylactic acid solution at a temperature between about 15° C. and about 25° C. after the heating step.

21. The process for producing the peroxylactic acid solution according to claim 1, wherein the heat of the mixture is maintained between about 30° C. and about 80° C. to allow the mixture to react to achieve the equilibrium peroxylactic acid solution.

22. The process for producing the peroxylactic acid solution according to claim 1, wherein the heat of the mixture is maintained between about 35° C. and about 70° C. to allow the mixture to react to achieve the equilibrium peroxylactic acid solution.

23. The process for producing the peroxylactic acid solution according to claim 1, wherein the heat of the mixture is maintained between about 40° C. and about 60° C. to allow the mixture to react to achieve the equilibrium peroxylactic acid solution.

24. The process for producing the peroxylactic acid solution according to claim 1, wherein the heat of the mixture is maintained between about 45° C. and about 55° C. to allow the mixture to react to achieve the equilibrium peroxylactic acid solution.

25. The process for producing the peroxylactic acid solution according to claim 1, wherein the peroxylactic acid in the peroxylactic acid solution exhibits less than 15% degradation over a period of at least 90 days while maintained at a temperature between about 15° C. and about 25° C.

26. The process for producing the peroxylactic acid solution according to claim 1, wherein the peroxylactic acid in the peroxylactic acid solution exhibits less than 10% degradation over a period of at least 90 days while maintained at a temperature between about 15° C. and about 25° C.

27. The process for producing the peroxylactic acid solution according to claim 1, wherein the pH of the equilibrium peroxylactic acid solution is between about 1.0 and 2.0.

28. A process of applying the peroxylactic acid solution produced according to claim 1 to a protein food product, wherein the peroxylactic acid solution is diluted to a concentration of the peroxylactic acid between about 5 ppm and about 2000 ppm before being applied to the protein food product.

29. The process of applying the peroxylactic acid solution according to claim 28, wherein the peroxylactic acid solution is applied to the protein food product by a food product application chosen from soaking, dipping, chilling, spraying, quenching, rinsing and washing.

30. The process of applying the peroxylactic acid solution according to claim 28, wherein the peroxylactic acid solution is applied to the protein food product chosen from red meat, poultry, pork, fish, eggs, seafood and nuts.

31. The process of applying the peroxylactic acid solution according to claim 28, wherein the peroxylactic acid solution applied to the protein food product reduces pathogens by $\log_{10}$ reduction of at least 0.5.

32. The process of applying the peroxylactic acid solution according to claim 28, wherein the peroxylactic acid solution is diluted to a concentration of the peroxylactic acid between about 20 ppm and about 1000 ppm before being applied to the protein food product.

\* \* \* \* \*